US00PP16366P2

(12) United States Plant Patent
Smith

(10) Patent No.: US PP16,366 P2
(45) Date of Patent: Mar. 21, 2006

(54) ***ASTER* PLANT NAMED 'YODAYDREAM'**

(50) Latin Name: *Aster hybrida*
Varietal Denomination: Yodaydream

(75) Inventor: Mark A. Smith, Fort Myers, FL (US)

(73) Assignee: Yoder Brothers, Inc., Barberton, OH (US)

( * ) Notice: Subject to any disclaimer, the term of this patent is extended or adjusted under 35 U.S.C. 154(b) by 28 days.

(21) Appl. No.: 11/045,987

(22) Filed: Jan. 28, 2005

(51) Int. Cl.
*A01H 5/00* (2006.01)

(52) U.S. Cl. ..... Plt./355

(58) Field of Classification Search ..... Plt./355
See application file for complete search history.

*Primary Examiner*—Kent Bell
(74) *Attorney, Agent, or Firm*—C. A. Whealy

(57) ABSTRACT

A new and distinct cultivar of *Aster* plant named 'Yodaydream', characterized by its uniform, outwardly spreading and mounded plant habit; freely branching growth habit; dark green-colored foliage; uniform flowering habit; natural flowering season around September 3$^{rd}$; large daisy-type inflorescences with violet-colored ray florets; and good garden performance.

1 Drawing Sheet

Botanical designation: *Aster hybrida.*
Cultivar denomination: 'Yodaydream'.

BACKGROUND OF THE INVENTION

The present Invention relates to a new and distinct cultivar of *Aster* plant, botanically known as *Aster hybrida* and hereinafter referred to by the name 'Yodaydream'.

The new *Aster* is a product of a planned breeding program conducted by the Inventor in Alva, Fla. The objective of the program is to develop new potted *Aster* cultivars that have a uniform plant growth habit, good vigor and strong branching habit, numerous inflorescences, desirable inflorescence form and floret colors, uniform flowering response and good postproduction longevity.

The new *Aster* originated from an open-pollination made by the Inventor in January, 2001 in Alva, Fla., of an unnamed proprietary *Aster hybrida* seedling selection, not patented, as the female, or seed, parent with an unknown *Aster hybrida* selection, not patented, as the male, or pollen, parent. The new *Aster* was discovered and selected by the Inventor in March, 2002, as a single flowering plant from within the resulting progeny of the stated open-pollination grown in a controlled environment in Alva, Fla.

The selection of this plant was based on its uniform plant growth habit, good vigor and strong branching habit, numerous inflorescences, desirable inflorescence form and floret colors, uniform flowering response and good postproduction longevity.

Asexual reproduction of the new *Aster* by vegetative tip cuttings was first conducted in Alva, Fla. in May, 2002. Asexual reproduction by cuttings has shown that the unique features of this new *Aster* are stable and reproduced true to type in successive generations.

SUMMARY OF THE INVENTION

The cultivar Yodaydream has not been observed under all possible environmental conditions. The phenotype may vary somewhat with variations in environment such as temperature, daylength, and/or light level, without, however, any variance in genotype.

The following traits have been repeatedly observed and are determined to be the unique characteristics of 'Yodaydream'. These characteristics in combination distinguish 'Yodaydream' as a new and distinct cultivar of *Aster:*

1. Uniform, outwardly spreading and mounded plant habit.
2. Freely branching growth habit.
3. Dark green-colored foliage.
4. Uniform flowering habit.
5. Natural flowering season around September 3$^{rd}$.
6. Large daisy-type inflorescences with violet-colored ray florets.
7. Good garden performance.

Plants of the new *Aster* can be compared to plants of the female parent selection. In side-by-side comparisons conducted in Alva, Fla., plants of the new *Aster* differed from plants of the female parent selection in the following characteristics:

1. Plants of the new *Aster* were larger than plants of the female parent selection.
2. Ray florets of plants of the new *Aster* were more blue in color than ray florets of plants of the female parent selection.

Plants of the new *Aster* can be compared to plants of the cultivar Ariel, disclosed in U.S. Plant Pat. No. 10,812. In side-by-side comparisons conducted in Alva, Fla., plants of the new *Aster* differed from plants of the cultivar Ariel in the following characteristics:

1. Plants of the new *Aster* were stronger, smaller and denser than plants of the cultivar Ariel.
2. Plants of the new *Aster* flowered about three weeks earlier than plants of the cultivar Ariel under natural season conditions.
3. Plants of the new *Aster* had larger inflorescences with more ray florets than plants of the cultivar Ariel.

4. Ray florets of plants of the new *Aster* were darker in color than ray florets of plants of the cultivar Ariel.

Plants of the new *Aster* can also be compared to plants of the cultivar Yomelody, disclosed in U.S. Plant Pat. No. 15,822. In side-by-side comparisons conducted in Alva, Fla., plants of the new *Aster* differed from plants of the cultivar Yomelody in the following characteristics:

1. Plants of the new *Aster* were more compact than plants of the cultivar Yomelody.
2. Plant habit of plants of the new *Aster* was more uniform than plant habit of plants of the cultivar Yomelody.
3. Plants of the new *Aster* flowered about three days earlier than plants of the cultivar Yomelody under natural season conditions.
4. Inflorescences of plants of the new *Aster* had fewer ray florets than inflorescences of plants of the cultivar Yomelody.
5. Ray floret color of plants of the new *Aster* did not fade whereas ray floret color of plants of the cultivar Yomelody faded with development.

BRIEF DESCRIPTION OF THE PHOTOGRAPHS

The accompanying colored photographs illustrate the overall appearance of the new *Aster* showing the colors as true as it is reasonably possible to obtain in colored reproductions of this type. Colors in the photographs may differ from the color values cited in the detailed botanical description which accurately describe the colors of the new *Aster*.

The photograph at the bottom of the sheet comprises a side perspective view of a typical flowering plant of 'Yodaydream' grown in a container.

The photograph at the top of the sheet comprises a close-up view of typical inflorescences of 'Yodaydream'.

DETAILED BOTANICAL DESCRIPTION

In the following description, color references are made to The Royal Horticultural Society Colour Chart, 1995 Edition, except where general terms of ordinary dictionary significance are used. The aforementioned photographs, following observations and measurements describe plants grown and flowered during the summer in Salinas, Calif., in an outdoor nursery and under conditions which approximate those generally used in commercial potted *Aster* production. During the production of these plants, day temperatures were about 21 to 24° C. and night temperatures were about 10 to 13° C. Two unrooted cuttings were directly stuck in 15-cm containers and exposed to long day/short night conditions for 18 days. After the plants were rooted, plants were exposed to natural season conditions.

Botanical classification: *Aster hybrida* cultivar Yodaydream.

Parentage:

*Female, or seed, parent.*—Unnamed proprietary *Aster hybrida* seedling selection, not patented.

*Male, or pollen, parent.*—Unknown *Aster hybrida* selection, not patented.

Propagation:

*Type.*—Terminal vegetative cuttings.

*Time to initiate roots.*—About ten days at 22° C.

*Time to produce a rooted cutting.*—About 16 to 18 days at 22° C.

*Root description.*—Fine, fibrous; white in color, close to 155D.

*Rooting habit.*—Freely branching.

Plant description:

*Appearance.*—Daisy-type potted *Aster*. Upright with lateral branches outwardly spreading; inverted triangle with uniformly mounded crown. Strong and freely branching growth habit with lateral branches potentially developing at every node; dense and full plants. Moderately vigorous.

*Plant height.*—About 26 cm.

*Plant width* (*single plant*).—About 29.5 cm.

*Lateral branches.*—Length: About 24 cm. Diameter: About 4 mm. Internode length: About 1.3 cm. Strength: Strong. Texture: Smooth, glabrous. Color: 144A.

*Foliage description.*—Arrangement: Alternate; simple; sessile. Length: About 5.2 cm. Width: About 9 mm. Shape: Linear. Apex: Acute. Base: Attenuate. Margin: Entire. Texture, upper and lower surfaces: Smooth, glabrous. Color: Developing foliage, upper and lower surfaces: 147A. Fully expanded foliage, upper surface: 147A; venation, 147B. Fully expanded foliage, lower surface: 147B; venation, 147B.

Inflorescence description:

*Appearance.*—Daisy-type terminal and axillary inflorescences with ligulate to linear-shaped ray florets. Disc and ray florets develop acropetally on a capitulum. Inflorescences not fragrant. Inflorescences face upright to outwardly.

*Flowering response.*—Under natural conditions, plants flower about September 3$^{rd}$. Uniform flowering habit.

*Inflorescence longevity.*—Inflorescences maintain good color and substance for about one week on the plant. Inflorescences persistent.

*Quantity of inflorescences.*—Freely flowering habit; about 30 open inflorescences per lateral branch.

*Inflorescence bud.*—Height: About 1.5 cm. Diameter: About 6 mm. Shape: Oval to elongate. Color: 85A.

*Inflorescence diameter.*—Large, about 4 cm.

*Inflorescence height.*—About 1.7 cm.

*Diameter of disc.*—About 1.4 cm.

*Receptacle diameter.*—About 1.3 cm.

*Receptacle height.*—About 1 cm.

*Ray florets.*—Shape: Ligulate to linear. Orientation: Initially upright, then about 85 to 90° from vertical. Aspect: Straight, mostly flat. Length: About 1.8 cm. Width: About 2 mm. Apex: Acute. Base: Acute. Margin: Entire. Texture: Smooth, glabrous; satiny. Number of ray florets per inflorescence: About 44 arranged in about two whorls. Color: When opening and fully opened, upper surface: Close to 85A; towards the base, 85B; color does not fade with development. When opening and fully opened, lower surface: Close to 85C to 85D.

*Disc florets.*—Arrangement: Massed at center of receptacle. Shape: Tubular, elongated. Apex: Five-pointed. Length: About 8 mm. Diameter, apex: About 2 mm. Diameter, base: Less than 1 mm. Number of disc florets per inflorescence: About 38. Color, immature: Close to 11A. Color, mature: Apex and mid-section: Close to 11B. Base: Close to 157B.

*Phyllaries.*—Quantity per inflorescence: About 32. Length: About 1 cm. Width: About 2 mm. Shape: Ligulate. Apex: Acute. Base: Truncate, fused. Margin: Entire. Texture, upper and lower surface: Smooth, glabrous. Color, upper and lower surfaces: 147A.

*Peduncles.*—Length: Terminal peduncle: About 4.3 cm. Third peduncle: About 6.2 cm. Diameter: About 1 mm. Angle to vertical: About 35 to 45° from vertical. Strength: Strong, flexible. Texture: Smooth, glabrous. Color: 146A.

*Reproductive organs.*—Androecium: Stamen quantity per floret: About five. Anther length: About 3 mm. Anther color: 12A. Pollen amount: Scarce. Pollen color: 12A. Gynoecium: Pistil quantity per ray floret: One. Pistil length: About 7 mm. Stigma shape: Bi-parted. Stigma color: 157A. Style length: About 4 mm. Style color: 157B. Ovary color: 157B. Seed/fruit: Seed and fruit production has not been observed.

Disease/pest resistance: Resistance to pathogens and pests common to *Asters* has not been observed on plants grown under commercial production conditions.

Garden performance: Plants of the new *Aster* have been observed to be rain and wind tolerant and to tolerate temperatures from 0 to more than 38° C.

It is claimed:

1. A new and distinct cultivar of *Aster* plant named 'Yodaydream', as illustrated and described.

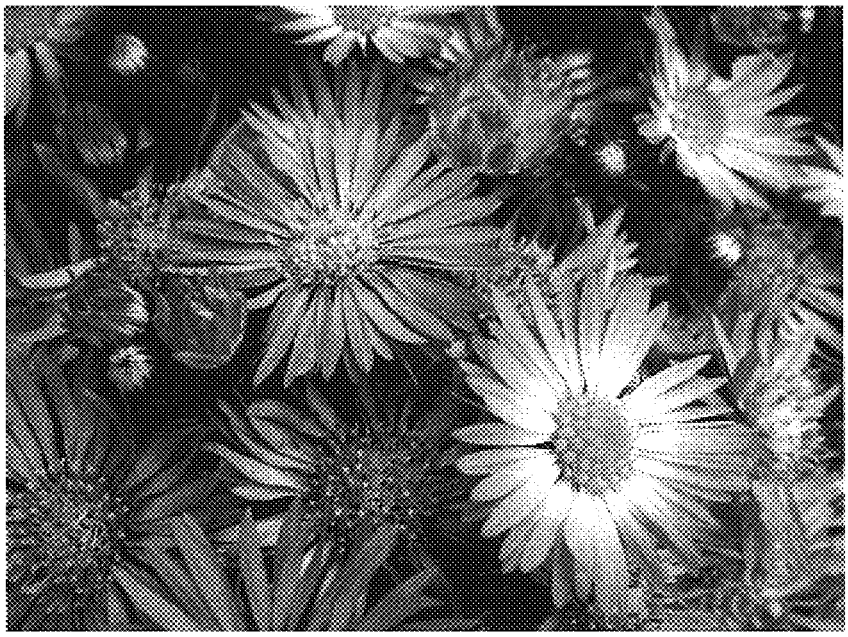
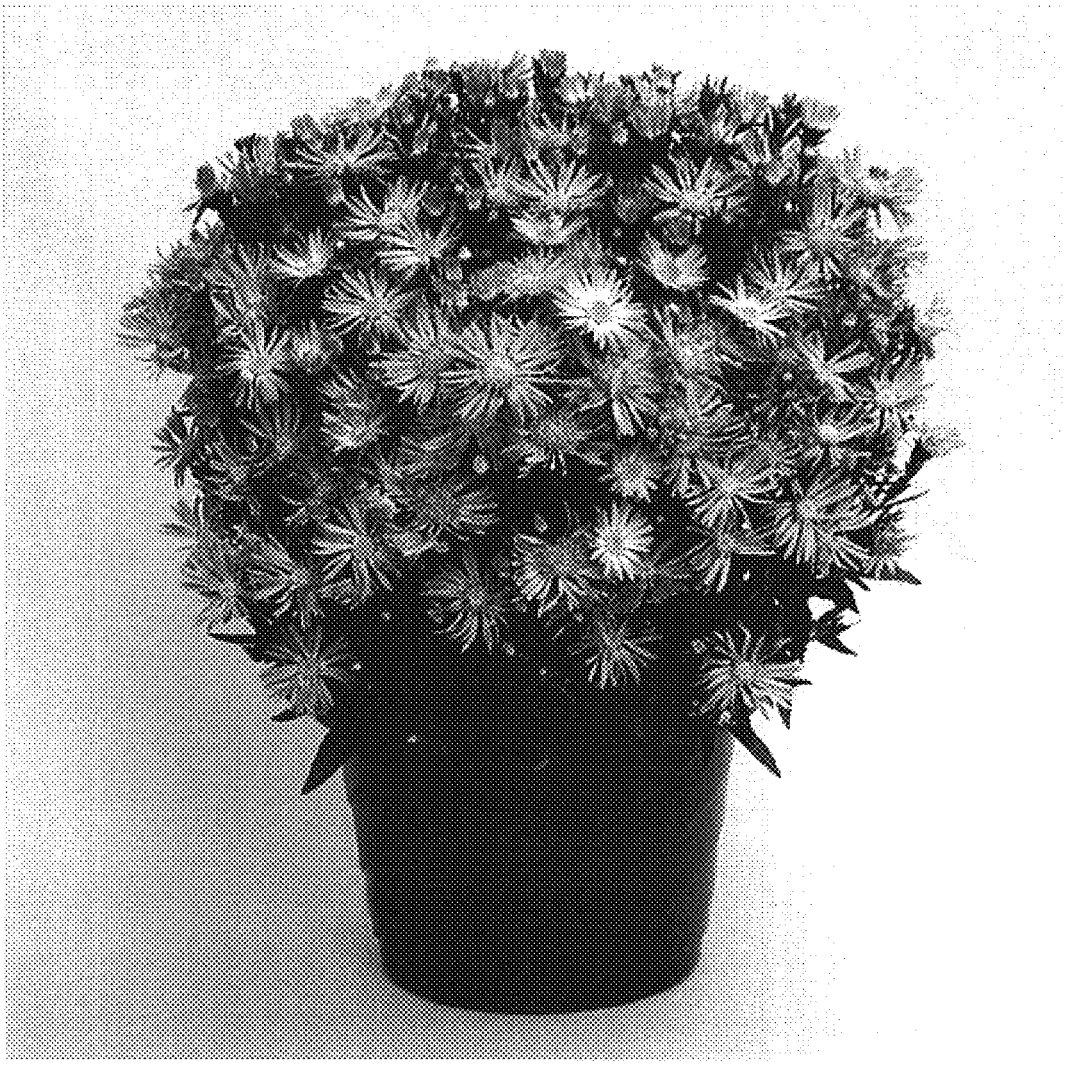

* * * * *